(12) United States Patent
Olson

(10) Patent No.: US 12,232,802 B2
(45) Date of Patent: Feb. 25, 2025

(54) PULMONARY VEIN ISOLATION BALLOON CATHETER

(71) Applicant: ST. JUDE MEDICAL, CARDIOLOGY DIVISION, INC., St. Paul, MN (US)

(72) Inventor: Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 277 days.

(21) Appl. No.: 17/357,991

(22) Filed: Jun. 25, 2021

(65) Prior Publication Data

US 2021/0393325 A1   Dec. 23, 2021

Related U.S. Application Data

(63) Continuation of application No. 16/466,934, filed as application No. PCT/US2017/064255 on Dec. 1, 2017, now Pat. No. 11,071,584.

(Continued)

(51) Int. Cl.
| | | |
|---|---|---|
| A61N 1/368 | (2006.01) |
| A61B 17/32 | (2006.01) |
| A61B 18/14 | (2006.01) |
| A61B 18/20 | (2006.01) |
| A61M 25/10 | (2013.01) |
| A61N 1/365 | (2006.01) |
| A61B 17/00 | (2006.01) |

(Continued)

(52) U.S. Cl.
CPC .. *A61B 18/1492* (2013.01); *A61B 17/320068* (2013.01); *A61B 18/20* (2013.01); *A61M 25/1002* (2013.01); *A61B 2017/003* (2013.01); *A61B 2017/320069* (2017.08); *A61B 2018/0022* (2013.01); *A61B 2018/00375* (2013.01); *A61B 2018/00577* (2013.01); *A61B 2018/00613* (2013.01); *A61B 2034/2051* (2016.02); *A61N 7/022* (2013.01)

(58) Field of Classification Search
CPC ........ A61B 18/1492; A61B 17/320068; A61B 18/20; A61B 2034/2051; A61B 2017/320069; A61B 2017/003; A61B 2018/0022; A61B 2018/00375; A61B 2018/00577; A61B 2018/00613; A61B 2018/00232; A61B 2018/00357; A61B 18/02; A61M 25/1002; A61N 7/022
See application file for complete search history.

(56) References Cited

U.S. PATENT DOCUMENTS

| | | |
|---|---|---|
| 8,277,444 B2 | 10/2012 | Arnold et al. |
| 8,382,689 B2 | 2/2013 | Sliwa et al. |

(Continued)

FOREIGN PATENT DOCUMENTS

| | | |
|---|---|---|
| WO | 2000562237 A2 | 9/2000 |
| WO | 2010042869 A1 | 4/2010 |

*Primary Examiner* — Brian T Gedeon
(74) *Attorney, Agent, or Firm* — Armstrong Teasdale LLP

(57) ABSTRACT

The instant disclosure relates to electrophysiology catheters for tissue ablation within a cardiac muscle. In particular, the instant disclosure relates to an electrophysiology catheter that conforms to a shape of a pulmonary vein receiving ablation therapy for a cardiac arrhythmia and produces a consistent tissue ablation line along a length and circumference of the pulmonary venous tissue.

16 Claims, 7 Drawing Sheets

Related U.S. Application Data

(60) Provisional application No. 62/432,045, filed on Dec. 9, 2016.

(51) Int. Cl.
*A61B 18/00* (2006.01)
*A61B 34/20* (2016.01)
*A61N 7/02* (2006.01)

(56) References Cited

U.S. PATENT DOCUMENTS

| | | |
|---|---|---|
| 8,449,538 B2 | 5/2013 | Long |
| 8,728,073 B2 | 5/2014 | McDaniel |
| 8,790,341 B2 | 7/2014 | Pappone et al. |
| 8,974,445 B2 * | 3/2015 | Warnking ............... A61N 7/022 601/3 |
| 9,289,606 B2 | 3/2016 | Paul et al. |
| 2004/0260277 A1 | 12/2004 | Maguire |
| 2006/0224153 A1 | 10/2006 | Fischell et al. |
| 2008/0086073 A1 * | 4/2008 | McDaniel .......... A61B 18/1492 606/191 |
| 2011/0184400 A1 | 7/2011 | Pageard |
| 2011/0270238 A1 | 11/2011 | Rizq et al. |
| 2014/0107427 A1 | 4/2014 | Chow et al. |
| 2016/0374754 A1 | 12/2016 | Asirvatham et al. |

* cited by examiner

PULMONARY VEIN ISOLATION BALLOON CATHETER

CROSS-REFERENCE TO RELATED APPLICATIONS

This application is a continuation of U.S. application Ser. No. 16/466,934, filed 5 Jun. 2019, which is the National Stage of International Application No. PCT/US2017/064255 filed 1 Dec. 2017, which claims the benefit of U.S. Provisional Application No. 62/432,045, filed 9 Dec. 2016.

BACKGROUND a. Field

The instant disclosure relates to catheters; in particular, catheters for conducting diagnostics or ablation therapy within a heart. In one embodiment, the instant disclosure relates to a catheter for treating cardiac arrhythmias by ablating in the vicinity of pulmonary venous tissue.

b. Background Art

The human heart routinely experiences electrical currents traversing its myocardial tissue. Just prior to each heart contraction, the heart depolarizes and repolarizes, as electrical currents spread through the myocardial tissue. In healthy hearts, the tissue of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to correct conditions such as atrial arrhythmia, including for example, ectopic atrial tachycardia, atrial fibrillation, and atrial flutter.

Typically in an intravascular procedure, a catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to myocardial tissue to create a lesion. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound.

The foregoing discussion is intended only to illustrate the present field and should not be taken as a disavowal of claim scope.

BRIEF SUMMARY

The instant disclosure relates to electrophysiology catheters for conducting diagnostics or tissue ablation within a heart. In particular, the instant disclosure relates to an electrophysiology catheter that conforms to a shape of a pulmonary vein receiving therapy for cardiac arrhythmias and produces a consistent tissue ablation line along a length and circumference of the pulmonary venous tissue.

Aspects of the present disclosure are directed to a medical device balloon apparatus. The apparatus including a distal portion with a first circumference, a proximal portion, and an intermediary portion. The proximal portion has a second circumference which is greater than the first circumference, and the intermediary portion has a varying circumference coupled between the proximal and distal portions of the ablation balloon. The distal portion includes a first circumferentially extending surface and the proximal portion includes a second circumferentially extending surface. Both of the first and second circumferentially extending surfaces extending tangential from a radial line extending off a longitudinal axis of the medical device balloon apparatus.

In one exemplary embodiment of the present disclosure, a system for treating atrial fibrillation is taught. The system includes a balloon delivery catheter with proximal and distal ends, and an ablation balloon coupled to the distal end of the balloon delivery catheter. The ablation balloon includes distal, proximal, and intermediary portions. The distal portion having a first circumference, and engages with an ostium of a pulmonary vein for aligning a longitudinal axis of the ablation balloon with a second longitudinal axis of the pulmonary vein. The proximal portion has a second circumference which is greater than the first circumference. The intermediary portion is coupled between the proximal and distal portions of the ablation balloon, and has a varying circumference. At least one of the proximal and intermediary portions of the ablation balloon engages with an antrum of the pulmonary vein along an uninterrupted length and circumference, and delivers a uniform ablation therapy to the pulmonary vein antrum.

In another embodiment of the present disclosure, a balloon catheter is disclosed for pulmonary vein isolation. The balloon catheter includes a catheter shaft, an ablation balloon, and tissue ablation means. The catheter shaft deploys an ablation balloon into a pulmonary vein, which is coupled to a distal end of the balloon delivery catheter. The ablation balloon deploys from an undeployed configuration and engages with a tissue wall of the pulmonary vein along an uninterrupted length and circumference of an antrum and ostia of the pulmonary vein. The tissue ablation means, in association with the ablation balloon, delivers a uniform ablation therapy around a circumference of the pulmonary vein antrum engaged by the ablation balloon. The ablation balloon also overcomes a biasing force exerted upon the ablation balloon by the catheter shaft by engaging with the ostia of the pulmonary vein to overcome the biasing force.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
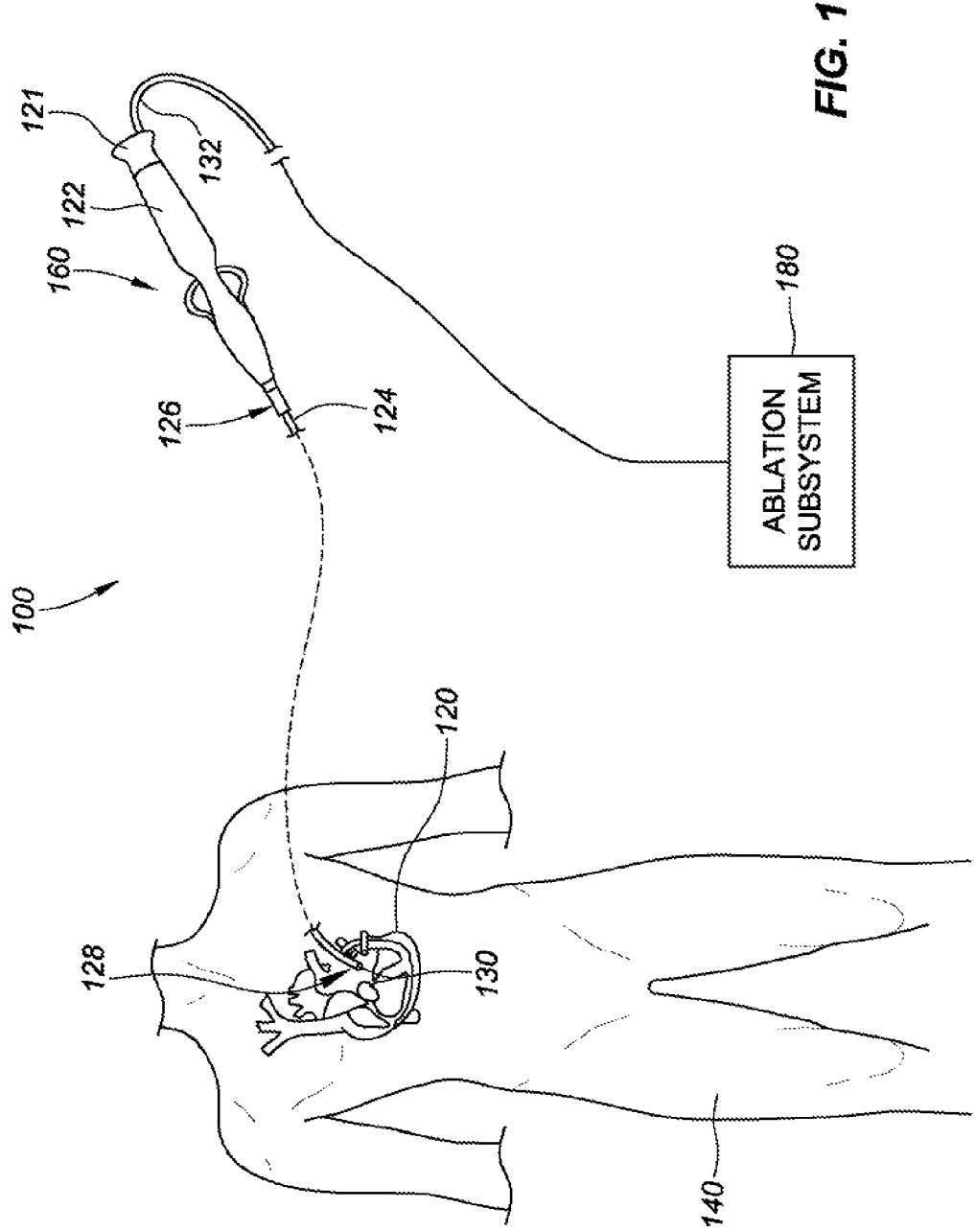
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for conducting diagnostics or tissue ablation within a heart. In particular, the instant disclosure relates to an electrophysiology catheter that conforms to a shape of a pulmonary vein receiving therapy for cardiac arrhythmias, and produces a consistent tissue ablation line along a length and circumference of the pulmonary venous tissue. Details of the various embodiments of the present disclosure are described below with specific reference to the figures.

Typically, ablation therapies have been delivered by making a number of individual ablations in a controlled fashion in order to form a lesion line. Such lesion lines are often desirably formed around/between the pulmonary veins in the left atrium of the heart which may introduce erratic electric signals into the heart. This type of ablation therapy requires precise positioning of the ablation catheter for optimal results. There are devices in development, or being commercialized, that attempt to achieve a sufficient block of ablations with minimal applications of energy. Existing designs range from diagnostic catheters with hoop and balloon mounted designs with energy applying features. Existing designs suffer from a lack of continuous contact around a circumference and length of the pulmonary vein during therapy deliver, resulting in inconsistent lesion lines and incomplete electrical signal blockage.

Referring now to the drawings wherein like reference numerals are used to identify similar components in the various views, FIG. 1 is a schematic and diagrammatic view of a catheter ablation system 100 for performing a tissue ablation procedure. In one example embodiment, tissue 120 comprises cardiac tissue within a human body 140. It should be understood, however, that the system may find application in connection with a variety of other tissue within human and non-human bodies, and therefore the present disclosure is not meant to be limited to the use of the system in connection with only cardiac tissue and/or human bodies.

Catheter ablation system 100 may include a catheter 160 and an ablation subsystem 180 for controlling an ablation therapy conducted by an ablation balloon 130 at a distal end 128 of the catheter 160. The ablation subsystem 180 can control the application of and/or generation of ablative energy including, for example, radio frequency (RF), direct current (DC), irreversible electroporation, cryoablation, laser, chemical, and high-intensity focused ultrasound. Example embodiments of such ablation subsystems are described in U.S. Pat. Nos. 8,449,538, 9,289,606, 8,382,689, and 8,790,341, which are hereby incorporated by reference as though fully set forth herein.

In the exemplary embodiment of FIG. 1, catheter 160 is provided for examination, diagnosis, and/or treatment of internal body tissue such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end 128 of the catheter shaft 124.

Ablation balloon 130 may be manipulated through vasculature of a patient 140 using handle 122 to steer one or more portions of shaft 124 and position the ablation balloon at a desired location (e.g., within a heart muscle). In various embodiments, the ablation balloon includes ablation elements (e.g., ablation electrodes, high intensity focused ultrasound ablation elements, super cooled/heated fluid, etc.) that when operated by ablation subsystem 180 ablates the tissue 120 in contact with the ablation balloon 130 (and in some cases tissue in proximity to the ablation balloon 130 may be ablated by conductive energy transfer through the blood pool and to the proximal tissue).

In various specific embodiments of the present disclosure, catheter 160 may include electrodes and one or more positioning sensors at a distal end 128 of catheter shaft 124 (e.g., electrodes and/or magnetic sensors). In such an embodiment, the electrodes acquire EP data relating to cardiac tissue 120, while the positioning sensor(s) generate positioning data indicative of the 3-D position of the ablation balloon 130. In further embodiments, the catheter 160 may further include other conventional catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 to ablation balloon 130. In other embodiments, the connector may also provide mechanical, electrical, and/or fluid connections for cables extending from other components in catheter system 100, such as, for example, a fluid source (when the catheter 160 comprises an irrigated catheter) and contact/pressure sensing circuitry. The connector 121 is conventional in the art and is disposed at a proximal end 126 of the catheter 160.

Handle 122 provides a location for a user to hold catheter 160 and may further provide steering or guidance for the shaft 124 within the body 140. For example, the handle 122 may include means to manipulate one or more steering wires extending through the catheter 160 to a distal end 128 of the shaft 124, thereby steering the shaft. The handle 122 is conventional in the art and it will be understood that the construction of the handle may vary. In other embodiments, control of the catheter 160 may be automated by robotically driving or controlling the catheter shaft 124, or driving and controlling the catheter shaft 124 using a magnetic-based guidance system.

Catheter shaft 124 is an elongated, tubular, and flexible member configured for movement within a patient's body 140. The shaft supports an ablation balloon 130 at a distal end 128 of catheter 160. The shaft 124 may also permit transport, delivery and/or removal of fluids (including irrigation fluids, cryogenic ablation fluids, and body fluids), medicines, and/or surgical tools or instruments. The shaft 124, which may be made from conventional materials used for catheters, such as polyurethane, defines one or more lumens configured to house and/or transport electrical conductors, fluids, and/or surgical tools. The catheter may be introduced into a blood vessel or other structure within the body 140 through a conventional introducer sheath.

In an exemplary cardiac ablation therapy, to correct for atrial arrhythmia, the introducer sheath is introduced through a peripheral vein (typically a femoral vein) and advanced into the right atrium, in what is referred to as a transeptal approach. The introducer sheath then makes an incision in the fossa ovalis (the tissue wall between the left and right atriums), and extends through the incision in the fossa ovalis to anchor the introducer sheath in the fossa ovalis. The ablation catheter 160 may then be extended through a lumen of the introducer sheath into the left atrium. Catheter shaft 124 of ablation catheter 160 may then be steered or guided through the left atrium to position an ablation balloon 130 into a desired location within the left atrium such as a pulmonary vein.

During cardiac ablation therapy, it is desirable to align the centerline of ablation balloon 130 with a centerline of an antral and/or proximal ostia of a pulmonary vein in which the ablation therapy is to take place. Alignment of the ablation balloon is particularly difficult in many embodiments due to the transeptal approach through the fossa ovalis which causes the shaft 124 to be naturally biased toward a right-side of a patient's body 140. This bias places an additional torque on ablation catheter system 100, which may result in the ablation balloon, after placement within the pulmonary vein, to bias away from the centerline of the pulmonary vein. Where the ablation balloon 130 is deployed away from the centerline of the pulmonary vein, the deployment may result in uneven contact pressure and corresponding uneven pulmonary vein tissue wall stress. It has been discovered that contact area and tissue strain are associated with decreased ablation therapy efficacy. Aspects of the present disclosure improve the efficacy of ablation therapy by more effectively positioning the ablation balloon 130 circumferential with a centerline of the pulmonary vein. In more specific embodiments, the deployed ablation balloon 130 further improves ablation therapy efficacy by having improved contour mapping to the pulmonary vein, thereby deploying and engaging the pulmonary vein along an extended and uninterrupted length and circumference of the ablation balloon 130.

Figure 2:
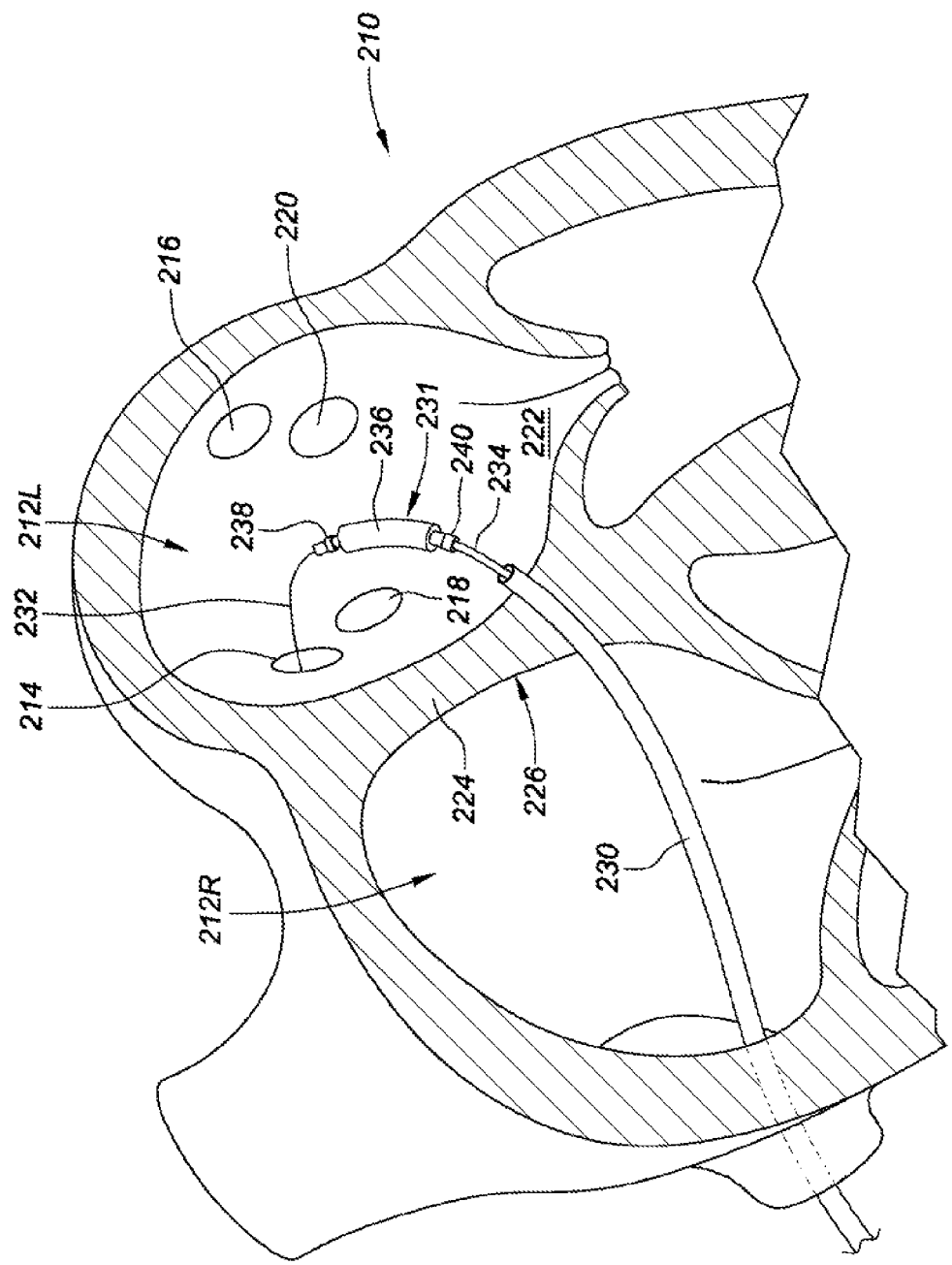
FIG. 2 is a cross-sectional front-view of a portion of a heart with an ablation balloon catheter locating a pulmonary vein from within the left atrium, consistent with various aspects of the present disclosure.

FIG. 2 is a cross-sectional front-view of a portion of a heart 210 with an ablation balloon catheter 231 locating a pulmonary vein (e.g., 214, 216, 218, and 220) from within left atrium 212L, consistent with various aspects of the present disclosure. Such an approach may be used for performing atrial fibrillation therapy. As shown in FIG. 2, the cardiac muscle 210 includes two upper chambers called the left atrium 212L and right atrium 212R, and two lower chambers called the left ventricle and right ventricle (partially visible).

Aspects of the present disclosure are directed to ablation therapies in which tissue in (or adjacent to) pulmonary veins 214, 216, 218, and 220, which form conductive pathways for electrical signals traveling through the tissue, is destroyed in order to electrically isolate sources of unwanted electrical impulses (arrhythmiatic foci) located in the pulmonary veins. By either destroying the arrhythmiatic foci, or electrically isolating them from the left atrium 212L, the cause of atrial fibrillation can be reduced or eliminated.

As shown in FIG. 2, an ablation balloon catheter 231 may be introduced into the left atrium 212L by an introducer sheath 230. A guidewire 232 and a steerable portion of the catheter shaft 234 may guide the ablation balloon 236 once introduced into the left atrium 212L by the introducer sheath 230. Optionally, the ablation balloon catheter 231 may include mapping electrodes 240 and 238 at proximal and distal ends, respectively, of ablation balloon 236. In operation, introducer sheath 230 has its distal end positioned within left atrium 212L. As shown in FIG. 2, a transeptal approach may be utilized in which introducer sheath 230 is introduced through a peripheral vein (typically a femoral vein) and advanced to right atrium 212R. The introducer sheath 230 makes a small incision into the fossa ovalis 226 which allows the distal end of the introducer sheath 230 to enter the left atrium 212L (through the transeptal wall 224) and to anchor itself to the wall of the fossa ovalis 226.

Ablation balloon catheter 231 may also be introduced into left atrium 212L through the arterial system. In that case, introducer sheath 230 is introduced into an artery (such as a femoral artery) and advanced retrograde through the artery to the aorta, the aortic arch, and into the left ventricle. The ablation balloon catheter 231 is then extended from within a lumen of the introducer sheath 230 to enter the left atrium 212L through mitral valve 222.

Once introducer sheath 230 is in position within left atrium 212L, steerable ablation balloon catheter 231 is advanced out a distal end of the introducer sheath and toward one of the pulmonary veins (e.g., 214, 216, 218, and 220). In FIG. 2, the target pulmonary vein is right superior pulmonary vein 214. A guidewire 232 and a steerable portion 234 of the ablation balloon catheter are manipulated until the distal tip of the ablation balloon catheter is directed toward the ostium of the target pulmonary vein, after which the ablation balloon is extended at least partially into the pulmonary vein.

Carried near a distal end of ablation balloon catheter 231, ablation balloon 236 remains in a collapsed condition so that it may pass through introducer sheath 230, and enter target pulmonary vein 214. Once in position, the ablation balloon 236 is deployed, so that it engages and secures the ablation balloon catheter 231 in a position axial to the target pulmonary vein 214.

As optionally shown, the embodiment of FIG. 2 may include mapping electrodes 238 and 240. The mapping electrodes 238 and 240 may be ring electrodes that allow the clinician to perform a pre-deployment electrical mapping of the conduction potentials of the pulmonary vein 214. Although shown as being carried on ablation balloon catheter 231, mapping electrodes may alternatively be carried on-board a separate electrophysiology catheter (e.g., such as on-board a loop catheter).

To ablate the tissue, once deployed, ablation balloon 236 may electrically conduct a DC energy current into the targeted tissue of the pulmonary vein 214. In other embodiments, the ablation balloon 236 may transmit radio-frequency energy to ablate the target tissue. In yet other embodiments, the ablation balloon 236 may deliver one or more of the following energies to the targeted tissue: cryoablation, laser, chemical, and high-intensity focused ultrasound, among others.

Figure 3:
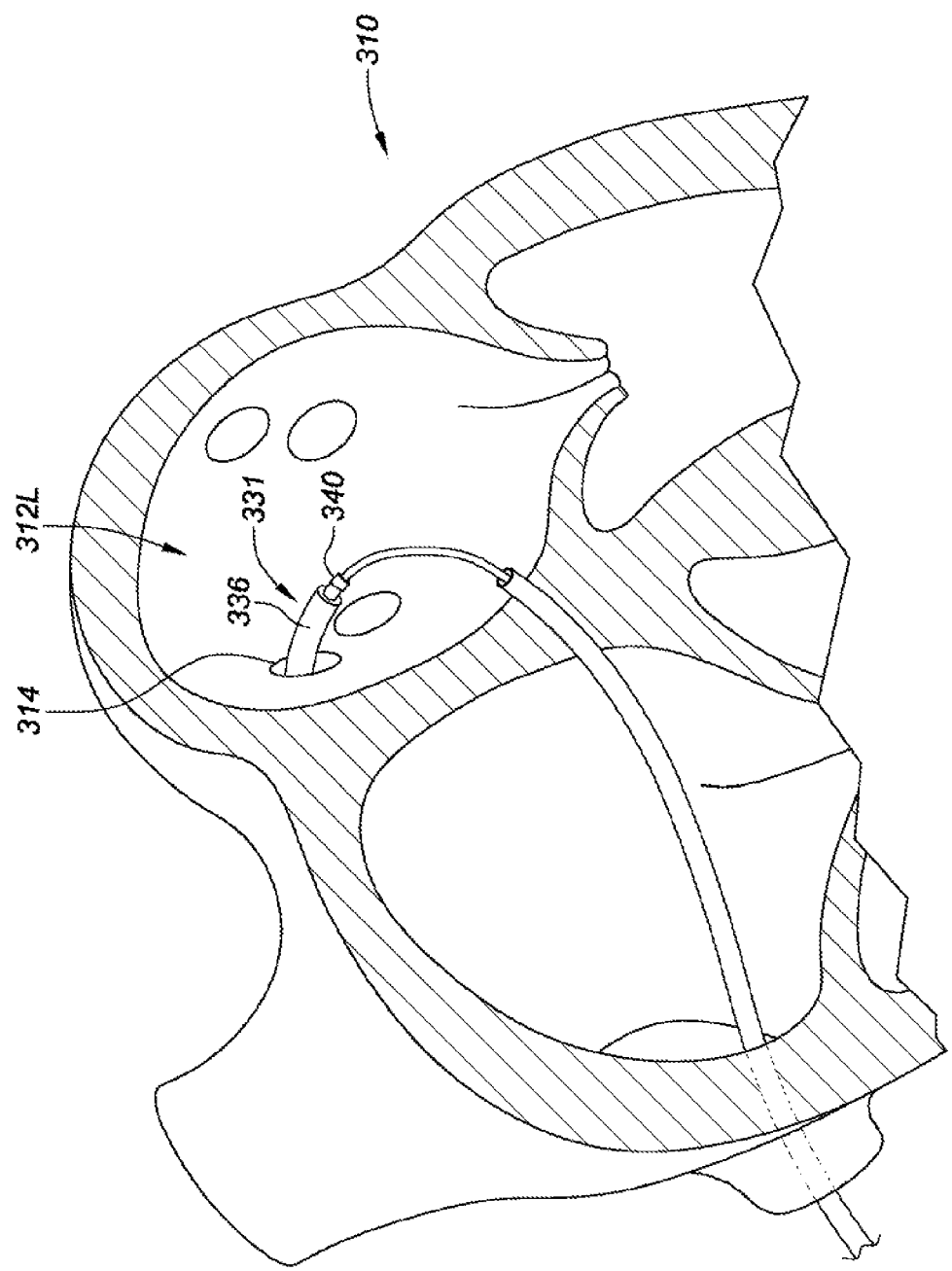
FIG. 3 is a cross-sectional front-view of a left atrium with an ablation balloon catheter positioned within a pulmonary vein, consistent with various aspects of the present disclosure.

FIG. 3 shows an ablation balloon catheter 331 including an ablation balloon 336 advanced into the ostium of pulmonary vein 314. As the ablation balloon catheter 331 enters the pulmonary vein 314, mapping may be conducted using electrodes 338 (hidden from view) and 340 in order to verify proper location prior to deployment of the ablation balloon 336.

It has been discovered that proper positioning of the ablation balloon within the pulmonary vein is critical to the efficacy of an ablation therapy. For example, if the ablation balloon is not centered axially within the pulmonary vein when inflated, a portion of the ablation balloon may not contact a portion of the pulmonary vein circumference. This portion of non-lesioned tissue will allow for the continued conduction of electrical signals through the pulmonary vein and into the left atrium 312L of the heart 310. Non-lesioned tissue greatly impedes the efficacy of the lesioned tissue to limit the flow of stray electrical signals that cause arrhythmias. Moreover, the ill-centered position and uneven pressure of the ablation balloon within the pulmonary vein 314 may overly-stress pulmonary vein tissue that is in contact with the ablation balloon 336 when inflated, and may also reposition the pulmonary vein closer to structures (e.g., phrenic and esophageal nerves) that can be damaged by a nominal lesion depth of the ablation therapy. The Applicant has discovered that overly-straining the pulmonary vein tissue results in thin tissue and a deeper lesion than desired; similarly, under-straining the pulmonary vein tissue results in thicker tissue and a shallower lesion than desired—all of which decreases ablation therapy efficacy. Specifically, stressed tissue is less likely to evenly ablate and may even exhibit increased thermal capacity capability, therefore being capable of absorbing increased ablation energy before necrosis. Accordingly, aspects of the present disclosure improve the fit of the ablation balloon 336 within the pulmonary vein 314 with an ablation balloon profile that betters conforms to the contours of the pulmonary vein between antral and ostial portions thereof. This improved conformance between the inflated ablation balloon 336 and pulmonary vein 314 results in improved ablation therapy efficacy, and the reduced likelihood that follow-up ablation procedures will be necessary.

Figure 4:
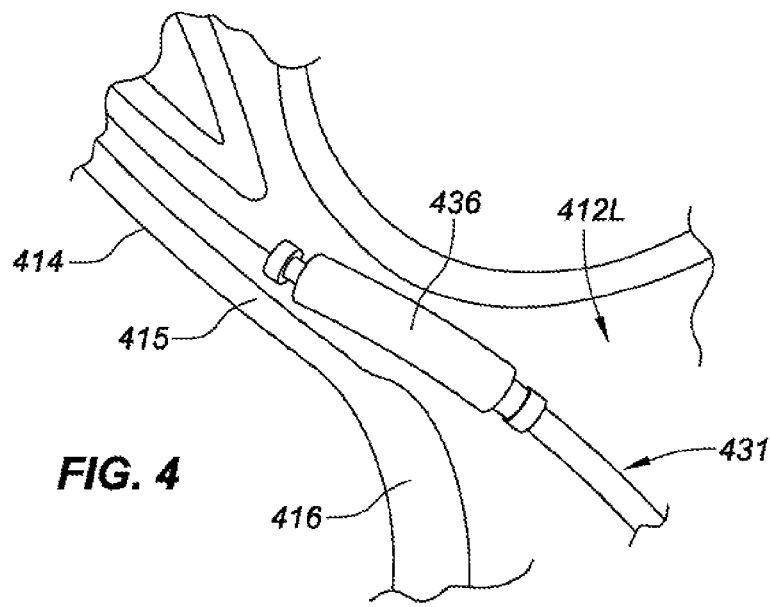
FIG. 4 is a cross-sectional front-view of portions of a left atrium and a pulmonary vein with an ablation balloon catheter positioned therein, prior to deployment of the ablation balloon, consistent with various aspects of the present disclosure.
Figure 7A:
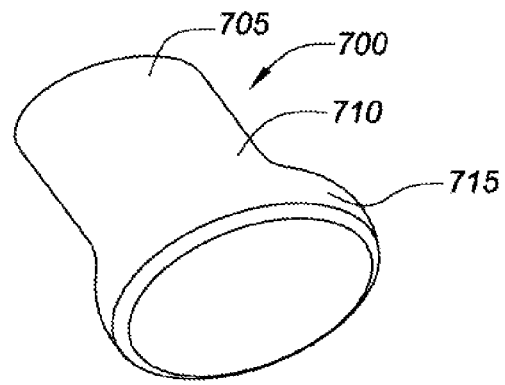
FIG. 7A is an isometric rear view of an ablation balloon, consistent with various aspects of the present disclosure.
Figure 7B:
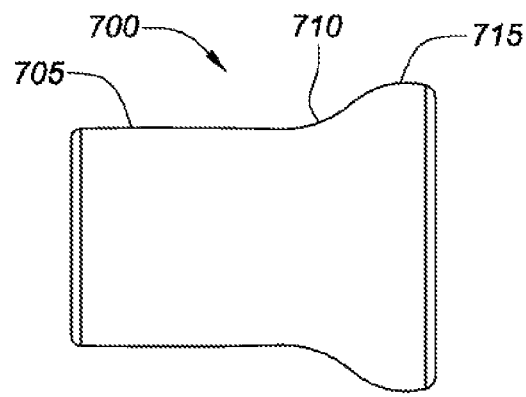
FIG. 7B is a top view of the ablation balloon of FIG. 7A, consistent with various aspects of the present disclosure.
Figure 7C:
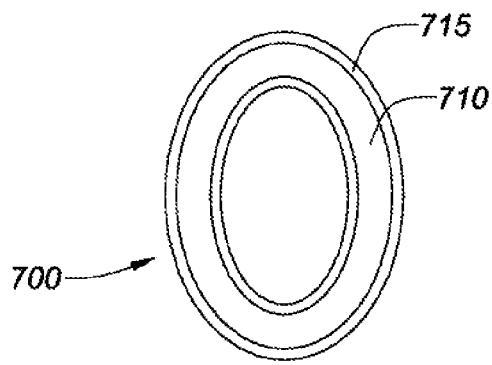
FIG. 7C is a front view of the ablation balloon of FIG. 7A, consistent with various aspects of the present disclosure.

FIG. 4 is a cross-sectional front-view of portions of a left atrium 412L and a pulmonary vein 414 with an ablation balloon catheter 431 positioned therein, prior to deployment of the ablation balloon 436, consistent with various aspects of the present disclosure. As shown in FIG. 4, the ablation balloon 436 is in position within the pulmonary vein 414 prior to balloon deployment. In one embodiment of the present disclosure, the proper location of the ablation balloon may be determined/verified by mapping, prior to deployment of the ablation balloon. As shown in FIG. 4, ostial and antral portions of the pulmonary vein, 415 and 416 respectively, are irregular and varying in shape along both a longitudinal length and a cross-section of the pulmonary vein. Importantly, it has been discovered that many pulmonary veins exhibit an oval cross-sectional shape, as opposed to circular. Where ablation balloons are substantially circular, during inflation certain portions of the oval cross-sectional shape of the pulmonary vein may be overly stressed, while other portions of the pulmonary vein do not contact the ablation balloon limiting efficacy of the ablation therapy. Accordingly, aspects of the present disclosure are directed to an ablation balloon with a substantially oval shape (e.g., as shown in FIGS. 7A-C). Such embodiments minimize and unify wall stress along a circumference of the pulmonary veinous tissue.

Figure 5:
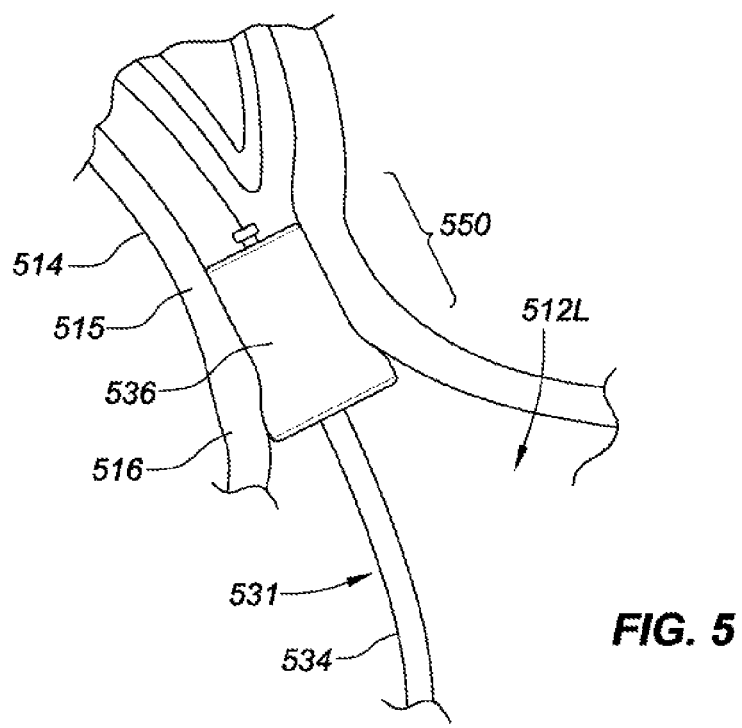
FIG. 5 is a cross-sectional front-view of a pulmonary vein with an ablation balloon catheter deployed therein, consistent with various aspects of the present disclosure.

FIG. 5 shows expanded ablation balloon 536 engaged between ostial portion 515 and antral portion 516 of target pulmonary vein 514. The expanded shape of the ablation balloon 536 has three distinct portions, as further discussed in relation to FIGS. 6A-B, and 7A-C, designed to more precisely match the contours of the pulmonary vein. This distinct shape increases the surface area contact between the pulmonary vein and the expanded ablation balloon, which consequently greatly improves the efficacy of the ablation therapy (that relies on surface contact between the ablation balloon and pulmonary vein tissue). Without continuous contact along a circumference of the pulmonary vein, a continuous lesion along the circumference may not be formed. As a result, stray electrical signals (though likely decreased in strength) may still be able to travel between the pulmonary vein and left atrium 512L. Accordingly, the patient may still experience cardiac arrhythmias. As such, continuous contact along a diameter of the pulmonary vein is necessary to completely ablate the pulmonary vein tissue and to mitigate all electrical signal communication between the pulmonary vein and the left atrium. To achieve such continuous contact, the present disclosure teaches a multi-contour ablation balloon with at least three distinct portions for more effective ablation therapies.

In its expanded state shown in FIG. 5, ablation balloon 536 engages inner walls of target pulmonary vein 514. Through one or more ablation processes mentioned above, the ablation balloon produces a circumferential zone of ablation 550 along the inner wall of the pulmonary vein between ostial 515 and antral 516 portions. The ablation zone electrically isolates the target pulmonary vein from left atrium 512L. To the extent that arrhythmiatic foci were located within the ablation zone, the arrhythmiatic foci are destroyed. To the extent the arrhythmiatic foci are located in the target pulmonary vein on the opposite side of the ablation zone from the left atrium, the electrical impulses produced by those foci are blocked or inhibited by the ablation zone.

In a typical ablation therapy, pulmonary veins are treated in accordance to their likelihood of having an arrhythmiatic foci. Often, all pulmonary veins are treated. The processes as described for right superior pulmonary vein 514 are similar for each of the three other pulmonary veins 516, 518, and 520.

Once ablation therapy is complete, ablation balloon 536 may be contracted and ablation balloon catheter 531 may be retracted back into introducer sheath 330 (as shown in FIG. 3). An electrophysiology catheter, or electrodes proximal and distal to the ablation balloon, may be used to verify the efficacy of the therapy prior to removal of the ablation balloon catheter 531. In various embodiments of the present disclosure, additional electrodes may also be positioned on a surface of the ablation balloon 536, either alone, or in conjunction with the electrodes proximal and distal the ablation balloon.

Ablation balloons have been developed for a variety of different applications and take a number of different forms. Aspects of the present disclosure may utilize ablation balloons of various types and different mechanical construction. The ablation balloons may be either of a conductive or a nonconductive material and can be either self-erecting or mechanically erected, such as through the use of an internal balloon. In one example embodiment, a lumen extending through a length of a shaft 534 of the ablation balloon catheter 531 may inject a fluid into the ablation balloon which exerts a radial force on the ablation balloon and thereby expands the balloon into an erect configuration (as shown in FIG. 5).

In certain specific embodiments, an ablation balloon may consist of non-compliant material. In such embodiments, over-expansion of a distal portion of the balloon near an ostial portion of the pulmonary vein tissue wall may be prevented where the proximal portion of the balloon has come into contact with an antral portion of the pulmonary vein tissue wall.

Figure 6A:
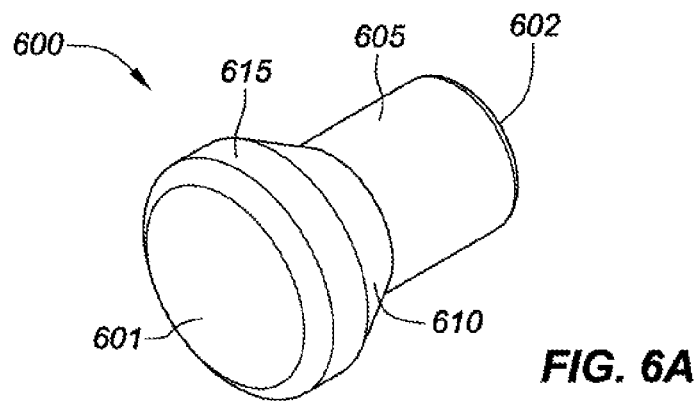
FIG. 6A is an isometric side view of an ablation balloon, consistent with various aspects of the present disclosure.
Figure 6B:
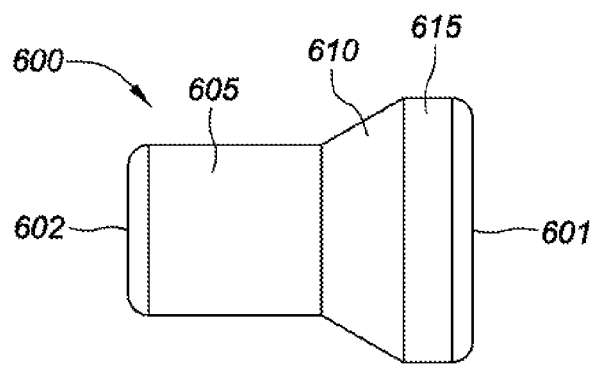
FIG. 6B is a top view of the ablation balloon of FIG. 6A, consistent with various aspects of the present disclosure.

FIGS. 6A and 6B are isometric side and top views, respectively, of an ablation balloon 600, consistent with various aspects of the present disclosure. As shown in FIGS. 6A and 6B, the ablation balloon includes three distinct portions that are designed to improve the amount of surface area of the ablation balloon contacting the interior of the pulmonary vein. A first portion 605 is designed to mate with an ostial portion of the pulmonary vein. An intermediary portion 610 similarly mates to a transitional portion of the pulmonary vein between the ostial and antral portions. A second portion 615 at a proximal end 601 of the ablation balloon mates to an antral portion of the pulmonary vein. By including three distinct contours along a length of the ablation balloon, the ablation balloon is better suited to conform to/with the contours of the pulmonary vein. As discussed above, contouring the length of the deployed ablation balloon to better contact the pulmonary vein is critical to the efficacy of the ablation therapy which requires contact between the pulmonary vein tissue and the ablation balloon 600. To improve insertion and withdraw characteristics of the ablation balloon catheter, the proximal end 601 and distal end 602 of the ablation balloon 600 may also include chamfers or radiuses to minimize sharp corners on the ablation balloon which may catch on an antral portion of the pulmonary vein when being inserted or on the introducer sheath when being retracted into a lumen of the sheath.

In one example application of ablation balloon 600 of FIGS. 6A and 6B, the shape of the ablation balloon may be tailor fit for a specific patient based on measurements (e.g., ultrasonic images, magnetic resonance images, etc.) of the patient's pulmonary vein and entrance thereto. Specifically, based on the measurements of the patient, a shape along the longitudinal axis of the ablation balloon 600 may be selected that mimics the shape of the pulmonary vein (and in some embodiments may vary along a length of the longitudinal axis). Similarly, the diameters of the various portions of the ablation balloon 600, including a first portion 605, and an intermediary portion 610 may vary over a length. For example, the intermediary portion 610 varies over a length to accommodate an antral portion of a target pulmonary vein as it intersects with the left atrium.

Figure 6C:
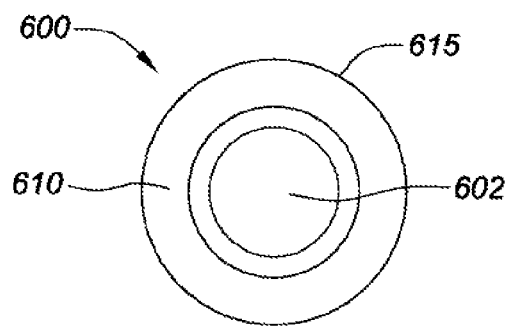
FIG. 6C is a front view of the ablation balloon of FIG. 6A, consistent with various aspects of the present disclosure.

As shown in FIGS. 6A-6C, and consistent with various embodiments of the present disclosure, a first portion 605 of ablation balloon 600 can be inserted into a pulmonary vein, and (when inflated therein) comes into contact with a length of an ostial portion of the vein. As shown in FIG. 6A, the first portion 605 of the ablation balloon 600 can be of a substantially consistent diameter along a longitudinal axis as the pulmonary vein ostia often maintains a fairly consistent diameter. Intermediary portion 610, when inflated within the pulmonary vein, can come into contact with a length of an antral portion of the pulmonary vein. Due to the antral portion of the pulmonary vein being located between a small diameter of the ostial portion of the pulmonary vein and a large diameter associated with an intersection between the pulmonary vein and left atrium, the antral portion often exhibits a varying diameter over a longitudinal axis of the vein. In some pulmonary veins, this varying diameter may be substantially linear as shown by the intermediary portion 610, as shown in FIG. 6B; in others, the intermediary portion may appear as a radius. The intermediary portion may also prevent over insertion of the ablation balloon 600 into the pulmonary vein. In one specific example, the ablation balloon 600 may be (partially) inflated before being inserted into the pulmonary vein. In such a case, the intermediary portion 610 (and/or second portion 615) acts as a hard-stop upon contacting the antral portion of the pulmonary vein.

In further example embodiments, ablation balloon 600 may be specific to a particular pulmonary vein. For example, various studies have determined average, maximum, and minimum pulmonary vein diameters across various patient demographics (see Table 1 below). Using such data, ablation balloons for each of the pulmonary veins may be created and swapped out during a therapeutic procedure for atrial fibrillation patients, for example; increasing efficacy of the ablation procedure. Various other parameters of a pulmonary vein may also be considered to tailor custom therapeutic solutions, thereby improving contact between each pulmonary vein and ablation balloon 600. In one specific example, where a range of diameters of a pulmonary vein ostia (e.g., right superior pulmonary vein) are between 15 and 20 millimeters, first portion 605 of the ablation balloon 600 may have a diameter around 19 millimeters to ensure contact (when inflated) between the pulmonary vein and the first portion 605 for most patients, while limiting the potential for damage to smaller diameter pulmonary veins which may be permanently damaged by excess wall stress on the pulmonary vein tissue. Moreover, when the tissue is experiencing an excess wall stress, the ablation therapy can suffer from decreased efficacy and consistency of ablation.

FIGS. 7A-C show isometric, top, and front views, respectively, of an ablation balloon 700, consistent with various aspects of the present disclosure. The ablation balloon consists of three distinct portions. A first portion 705 is designed to mate with an ostial portion of the pulmonary vein. An intermediary portion 710 includes a constantly varying outside diameter that mates to a transitional portion of the pulmonary vein between the ostial and antrum portions. A second portion 715 at a proximal end of the ablation balloon 700 includes a constantly varying outside diameter that mates to an antral portion of the pulmonary vein. By including three distinct contours along a length of the ablation balloon, the ablation balloon exhibits improved conformance to/with the contours of a target pulmonary vein. Importantly, as a further measure to improve the fit of the ablation balloon 700 within a pulmonary vein, a cross-sectional shape of the ablation balloon is substantially oval, which Applicant has discovered to more closely mimic the shape of a typical pulmonary vein. The substantially oval shape of the ablation balloon further facilitates uniform ablation therapy application within the pulmonary vein by improving the axial centering of the ablation balloon 700 within the pulmonary vein. Also, during inflation of the ablation balloon 700, the oval shape of the ablation balloon 700 can self-adjust (e.g., rotate) to properly mate with the curvature of the pulmonary vein.

In various embodiments of the present disclosure, an ablation balloon 700 is capable of conducting ablation therapy at more than one location of the ablation balloon. For example, energy can be delivered to a first portion 705, an intermediary portion 710, and a second portion 715 of the ablation balloon 700. In some embodiments, the first portion 705, the intermediary portion 710, the second portion 715, or combinations thereof may simultaneously conduct ablation therapy. For example, ablation energy can be applied in series (or in parallel) to the first portion 705 and the intermediary portion 710. In more specific embodiments, the amount of ablation therapy (e.g., energy transmitted to the tissue, and the length of therapy) conducted at a tissue location may be controlled individually.

In cryoablation specific applications of an ablation balloon catheter, a distal portion of the expanded ablation balloon centers the ablation balloon within a pulmonary vein and anchors it thereto. An intermediary portion and proximal portion are then cooled to deliver a cryoablation therapy to an antral portion of the pulmonary vein. Once the ablation therapy is complete, the ablation balloon is deflated and the ablation balloon is removed from the pulmonary vein.

In various embodiments of the present disclosure, an ablation balloon may include one or more (internal) balloons that may be independently inflated. In one exemplary embodiment, a first (internal) balloon positioned at a proximal end of the ablation balloon may be expanded to deliver ablation therapy circumferentially to the pulmonary vein antrum, and a second (internal) balloon positioned at a distal end of the ablation balloon may be expanded to deliver ablation therapy circumferentially to the pulmonary vein ostia. Such (internal) balloons can relate to portions of the ablation balloons in FIGS. 6 and 7 (e.g., first portion 705, intermediary portion 710, and second portion 715). In one specific embodiment, the one or more internal balloons may be encompassed by an external balloon.

One important benefit of the present disclosure is that ablation balloons, consistent herewith, are associated with decreased esophageal and phrenic nerve interaction with the pulmonary vein. Oftentimes, such interaction is caused by wall distortion due to expansion of the balloon within the pulmonary vein to a diameter greater than an internal diameter of the pulmonary vein. Preventing interaction between the pulmonary veins and the esophageal and phrenic nerves greatly decreases complications related to nerve damage from the ablation therapy.

In one specific application of ablation balloon 700 of FIGS. 7A-C, a first portion 705 (also referred to as a plug) may be plugged into a pulmonary vein, while an intermediary portion 710 (also referred to as a flared end—which may or may not include the second portion 715) conducts a cryoablation therapy. Such a design helps stabilize the balloon 700 within the pulmonary vein while improving contact around the pulmonary vein ostia.

Figure 8A:
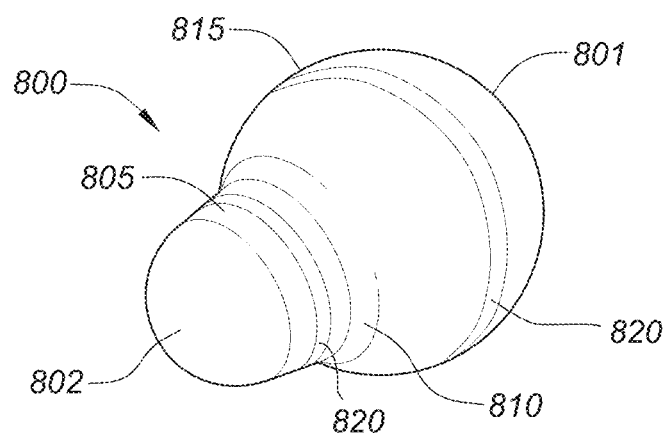
FIG. 8A is an isometric side view of an ablation balloon, consistent with various aspects of the present disclosure.
Figure 8B:
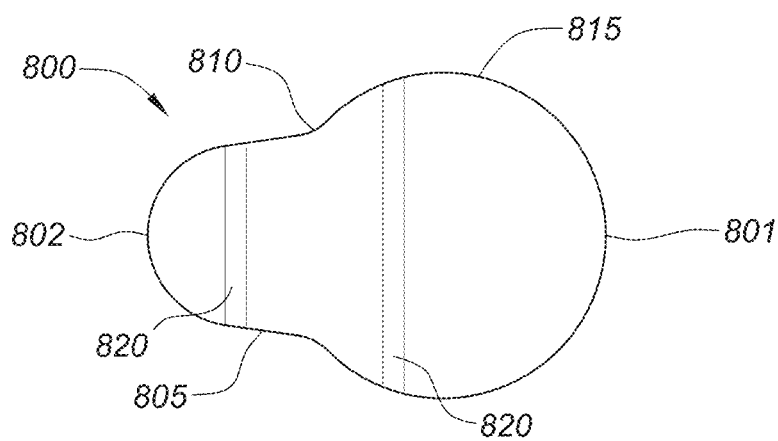
FIG. 8B is a top view of the ablation balloon of FIG. 8A, consistent with various aspects of the present disclosure.
Figure 8C:
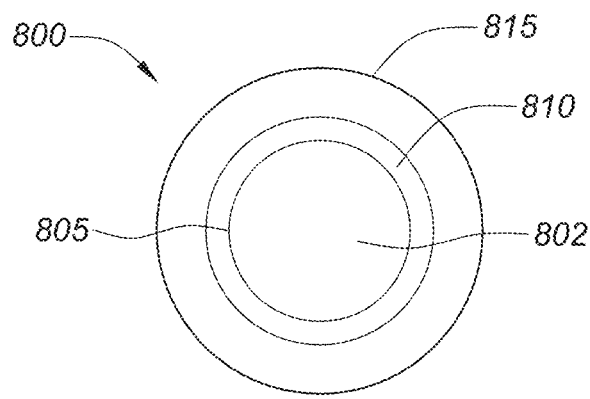
FIG. 8C is a front view of the ablation balloon of FIG. 8A, consistent with various aspects of the present disclosure.

FIGS. 8A-C show isometric, top, and front views, respectively, of an ablation balloon 800, consistent with various aspects of the present disclosure. The ablation balloon consists of five distinct portions. A distal portion 802 of the balloon 800 has a radial surface that extends into contact with a first longitudinally extending portion 805 designed to mate with an ostial portion of a pulmonary vein. The first longitudinally extending portion 805 may include one or more ablation elements 820. An intermediary portion 810 includes a (constantly) varying outside diameter that mates to a transitional portion of the pulmonary vein between the ostial and antrum portions. A second longitudinally extending portion 815 may be substantially spherical and extend to a proximal end 801 of the ablation balloon 800. The second longitudinally extending portion 815 may have a constantly varying outside diameter. In various embodiments, the second longitudinally extending portion 815 may mate with an antral portion of the pulmonary vein. The second longitudinally extending portion 815 may include one or more ablation elements 820. By utilizing these distinct contours along a length of the ablation balloon 800, the ablation balloon may exhibit improved conformance to/with the contours of a target pulmonary vein. In the present embodiment, the cross-sectional shape of the ablation balloon 800 is substantially peanut-shaped, which Applicant has discovered to more closely mimic the shape of a typical pulmonary vein.

Various embodiments of the present disclosure are directed to pulmonary vein isolation balloon designs for optimum therapy delivery. Specifically, the balloon designs disclosed herein may be configured to facilitate improved energy delivery by better alignment between the balloon and the antral and/or proximal ostia portions of the pulmonary vein. The various embodiments disclosed herein may be applied to any of the various balloon-based energy delivery means (such as those discussed in more detail above).

Many cardiac catheter applications utilize the fossa ovalis to enter the heart. Due to the geometry between the fossa ovalis and an entrance to the pulmonary veins in the left atrium, the catheter shaft will naturally be biased towards a left side of the patient, putting pull/torque on the cardiac catheter as it locates (and is positioned in contact with) the pulmonary vein (e.g., for pulmonary vein isolation ablation therapy procedures). This biasing force pulls the catheter shaft off the natural centerline of the pulmonary vein being targeted, causing a variation in the forces and contact surface area experienced between the balloon and the pulmonary vein walls. As an example, when the biasing force pulls an ablation balloon off the natural centerline of a target pulmonary vein, the contact surface area and force exerted by the balloon on the side of the pulmonary vein which receives the additional biasing force will be greater than the other side(s) of the balloon. As a result, the energy delivery of the catheter is tied to catheter position, and may be one contributor to therapy variation.

Various embodiments of the present disclosure may be directed to multi-shape balloons for ostial and antral coverage of pulmonary vein geometry (e.g., two or more geometries). Such multi-shape balloons may facilitate centering of the balloon within a pulmonary vein for uniform ablation therapy applications, for example. Also, such multi-shape balloons may enable energy delivery to both antral and ostial portions of the pulmonary vein simultaneously (due to the increased contact area)—thereby targeting linear and circumferential conduction paths. In yet further embodiments, the multi-shape balloons may target energy delivery to distal, mid, or proximal balloon surfaces. The multi-shape balloon may also utilize a distal length of the balloon to contact an ostial portion of the pulmonary vein, facilitating proper centering of the balloon in the pulmonary vein, while a proximal length of the balloon in contact with an antrum of the pulmonary vein conducts the ablation therapy.

A multi-shape balloon, such as that shown in FIGS. 5 and 6A-C, may be nested in a target pulmonary vein with a flare portion (also referred to as an intermediary portion 610) that contacts all around the pulmonary vein ostia and antrum. When the balloon is plugged into a pulmonary vein, a flared portion of the balloon may be cooled. Such a design facilitates balloon stabilization within the pulmonary vein via a first portion 605 (as shown in FIGS. 6A-C; also referred to as a plug) designed to mate with a circumference of the ostial portion of the pulmonary vein. In specific embodiments, a maximum flare of the balloon may be 23 millimeters in diameter with a 15 millimeter diameter distal end plug. In yet further more specific embodiments, the balloon may have an oval cross section to facilitate improved nesting in the pulmonary vein. It has been discovered that many pulmonary veins are oval (or at least the ostium/antral entrances of the pulmonary vein). Table 1 produced below shows the average pulmonary vein ostium diameters.

TABLE 1

Average Pulmonary Vein Ostium Diameters

|  | n | Maximum, mm | Minimum, mm | Ratio | Range, mm | Projected, mm |
| --- | --- | --- | --- | --- | --- | --- |
| Left superior | 38 | 18.7 ± 2.9 | 13.9 ± 3.7 | 1.4 ± 0.4 | 1.0-3.0 | 17.5 ± 2.9 |
| Left inferior | 38 | 15.9 ± 3.1 | 11.2 ± 3.1 | 1.5 ± 0.4 | 1.0-2.3 | 15.0 ± 2.7 |
| Both left | 76 |  |  | 1.5 ± 0.4* |  |  |
| Right superior | 42 | 18.8 ± 2.7 | 16.0 ± 2.0 | 1.2 ± 0.1 | 1.0-1.5 | 17.5 ± 2.1 |
| Righ inferior | 42 | 17.9 ± 2.9 | 15.1 ± 3.0 | 1.2 ± 0.2 | 1.0-1.7 | 16.9 ± 3.1 |
| Both right | 84 |  |  | 1.2 ± 0.1* |  |  |
| Left common | 4 | 27.3 ± 6.2 | 18.7 ± 6.7 | 1.6 ± 0.5 | 1.0-2.2 | 26.5 ± 4.8 |
| Right middle | 4 | 7.6 ± 3.1 | 5.6 ± 2.1 | 1.4 ± 0.4 | 1.0-2.0 | 7.0 ± 1.9 |

Dimensions of pulmonary vein ostia measures with MRA. For each pulmonary vein, the maximal and minimal ostium diameters were measured together with the projected diameter by using a 45° RAO or LAO view angle for the MRA images. The ratio between maximal and minimal ostium diameters is a measure of the ovality of the PV ostia.
*Differences in ovality were only significant between right and left pulmonary vein ostia (P <0.005). Table downloaded from http://circ.abajournals.org/ on Jun. 4, 2014

Using the average diameters in Table 1, above, balloon dimensions may be optimized to improve fit for a large percentage of the potential patient population. Further, with proper fit between the balloon and the pulmonary vein, the balloon will engage with, and hold in position better, within a pulmonary vein with minimal force during an ablation therapy, for example. Proper fit may also minimize and unify wall stress/distortion—providing more uniform reaction to various ablation energy types. With lesser stretching/distortion of the pulmonary vein due to the native spacing dimensions between the balloon and a target pulmonary vein, the potential for esophageal and phrenic nerve interaction may be greatly reduced.

Aspects of the present disclosure are directed to a medical device balloon apparatus. The apparatus includes a distal portion with a first circumference, a proximal portion, and an intermediary portion. The proximal portion has a second circumference which is greater than the first circumference, and the intermediary portion has a varying circumference coupled between the proximal and distal portions of the ablation balloon. The distal portion includes a first circumferentially extending surface and the proximal portion includes a second circumferentially extending surface. Both of the first and second circumferentially extending surfaces extend ing tangential from a radial line extending off a longitudinal axis of the medical device balloon apparatus.

In one exemplary embodiment of the present disclosure, a system for treating atrial fibrillation is taught. The system includes a balloon delivery catheter with proximal and distal ends, and an ablation balloon coupled to the distal end of the balloon delivery catheter. The ablation balloon includes distal, proximal, and intermediary portions. The distal portion has a first circumference, and engages with an ostium of a pulmonary vein for aligning a longitudinal axis of the ablation balloon with a second longitudinal axis of the pulmonary vein. The proximal portion has a second circumference which is greater than the first circumference. The intermediary portion is coupled between the proximal and distal portions of the ablation balloon, and has a varying circumference. At least one of the proximal and intermediary portions of the ablation balloon engages with an antrum of the pulmonary vein along an uninterrupted length and circumference, and delivers a uniform ablation therapy to the pulmonary vein antrum.

In another embodiment of the present disclosure, a balloon catheter is disclosed for pulmonary vein isolation. The balloon catheter includes a catheter shaft, an ablation balloon, and tissue ablation means. The catheter shaft deploys an ablation balloon into a pulmonary vein, which is coupled to a distal end of the balloon delivery catheter. The ablation balloon deploys from an undeployed configuration and engages with a tissue wall of the pulmonary vein along an uninterrupted length and circumference of an antrum and ostia of the pulmonary vein. The tissue ablation means, in association with the ablation balloon, delivers a uniform ablation therapy around a circumference of the pulmonary vein antrum engaged by the ablation balloon. The ablation balloon also overcomes a biasing force exerted upon the ablation balloon by the catheter shaft by engaging with the ostia of the pulmonary vein to overcome the biasing force.

Based upon the above discussion and illustrations, those skilled in the art will readily recognize that various modifications and changes may be made to the various embodiments without strictly following the exemplary embodiments and applications illustrated and described herein. For example, a deployed ablation balloon, consistent with aspects of the present disclosure, may consist of a number of varying geometries based on imaging data indicative of the internal dimensions of a patient's targeted pulmonary vein. In such an embodiment, the deployed ablation balloon engages the targeted pulmonary vein along an uninterrupted length and circumference of the ablation balloon to maximize the efficacy of the ablation therapy. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device balloon apparatus, the apparatus comprising an ablation balloon, the ablation balloon comprising:
   a semi-spherical distal portion with a first diameter;
   a semi-spherical proximal portion with a varying diameter along a longitudinal axis of the medical device balloon apparatus, the varying diameter being greater than the first diameter;
   a first longitudinally extending portion coupled to the distal portion; and
   a plurality of ablation elements, at least one ablation element of the plurality of ablation elements located on the semi-spherical proximal portion and at least one ablation element of the plurality of ablation elements located on the first longitudinally extending portion, the plurality of ablation elements configured to deliver tissue ablation therapy simultaneously on the semi-spherical proximal portion and the first longitudinally extending portion.

2. The apparatus of claim 1, further including an intermediate portion coupled between the proximal and distal portions, and having a varying diameter along a longitudinal axis of the medical device balloon apparatus.

3. The apparatus of claim 2, wherein the first longitudinally extending portion is positioned between the distal portion and the intermediate portion, the first longitudinally extending portion configured to mate with an ostial portion of a pulmonary vein.

4. The apparatus of claim 1, wherein the proximal portion is configured to mate with an antral portion of a pulmonary vein.

5. The apparatus of claim 1, wherein the distal portion is configured to axially align a longitudinal axis of the medical device balloon apparatus with a pulmonary vein by engaging with an ostium of the pulmonary vein.

6. The apparatus of claim 2, wherein at least one of the proximal and intermediate portions is configured to engage with an uninterrupted length and circumference of an antrum of a pulmonary vein and deliver a tissue ablation therapy along the antrum of the pulmonary vein.

7. The apparatus of claim 1, wherein the distal and intermediate portions are configured to engage with an ostium and antrum of a pulmonary vein along an uninterrupted length and circumference of the pulmonary vein.

8. The apparatus of claim 1, further including a catheter shaft coupled to a proximal end of the proximal portion, wherein the distal portion is configured to overcome a biasing force exerted upon the medical device balloon apparatus by the catheter shaft by engaging with an ostia of a pulmonary vein to overcome the biasing force.

9. The apparatus of claim 1, wherein the balloon apparatus is further configured to minimize and unify wall stress along a circumference of pulmonary vein tissue.

10. The apparatus of claim 1, further including first and second balloons that form the semi-spherical distal portion and the semi-spherical proximal portion of the balloon, the first and second balloons configured to be independently inflated, the first balloon positioned within the semi-spherical proximal portion and configured to deliver ablation therapy circumferentially to a pulmonary vein antrum, and the second balloon positioned within the semi-spherical distal portion and configured to deliver ablation therapy circumferentially to a pulmonary vein ostia.

11. A system for treating atrial fibrillation, the system comprising:
   a balloon delivery catheter including a proximal end and a distal end; and
   an ablation balloon coupled to the distal end of the balloon delivery catheter, the ablation balloon comprising:
      a semi-spherical distal portion with a first diameter, the distal portion configured to engage with an ostium of a pulmonary vein for aligning a first longitudinal axis of the ablation balloon with a second longitudinal axis of the pulmonary vein;
      a semi-spherical proximal portion with a varying diameter along a length of the first longitudinal axis of the ablation balloon, the varying diameter being greater than the first diameter, wherein a distal end of the semi-spherical proximal portion is coupled to a proximal end of the semi-spherical distal portion;
      a first longitudinally extending portion coupled to the distal portion; and
      a plurality of ablation elements, at least one ablation element of the plurality of ablation elements located on the semi-spherical proximal portion and at least one ablation element of the plurality of ablation elements located on the first longitudinally extending portion, the plurality of ablation elements configured to deliver tissue ablation therapy simultaneously on the semi-spherical proximal portion and the first longitudinally extending portion.

12. The system of claim 11, wherein the ablation balloon further includes:
   an intermediate portion coupled between the proximal and distal portions of the ablation balloon, with a varying circumference along the length of the first longitudinal axis;
   wherein the first longitudinally extending portion is positioned between the distal portion and the intermediate portion, wherein the first longitudinally extending portion is configured to mate with an ostial portion of the pulmonary vein;
   wherein at least one of the proximal and intermediate portions of the ablation balloon is configured to engage with an antrum of the pulmonary vein along an uninterrupted length and circumference, and deliver an ablation therapy to the pulmonary vein antrum.

13. The system of claim 11, wherein the ablation balloon includes first and second balloons that are configured to be independently inflated, the first balloon positioned within the proximal portion of the ablation balloon and further configured to deliver ablation therapy circumferentially to the pulmonary vein antrum, and the second balloon positioned within the distal portion of the ablation balloon and further configured to deliver ablation therapy circumferentially to the pulmonary vein ostia.

14. The system of claim 13, wherein the ablation balloon is further configured to minimize and unify wall stress along a circumference of pulmonary vein tissue.

15. The system of claim 12, wherein the ablation balloon consists of non-compliant material and is configured to prevent over-expansion of the distal portion in response to the intermediate portion of the balloon contacting an antrum of the pulmonary vein.

16. The system of claim 11, wherein the ablation balloon is configured to ablate tissue using one or more of the following: cryogenic fluid ablation, laser energy, radiofrequency energy, microwave energy, irreversible electroporation, chemical reaction, and high-intensity focused ultrasound.

* * * * *